United States Patent [19]

Sinofsky

[11] Patent Number: 4,929,246

[45] Date of Patent: May 29, 1990

[54] METHOD FOR CLOSING AND SEALING AN ARTERY AFTER REMOVING A CATHETER

[75] Inventor: Edward L. Sinofsky, Reading, Mass.

[73] Assignee: C. R. Bard, Inc., Murray Hill, N.J.

[21] Appl. No.: 263,277

[22] Filed: Oct. 27, 1988

[51] Int. Cl.$^5$ ............................................. A61B 17/36
[52] U.S. Cl. ........................................... 606/8; 606/3; 606/15
[58] Field of Search ............... 128/303.1, 395–398; 606/3, 8, 14, 15

[56] References Cited

U.S. PATENT DOCUMENTS

| | | | |
|---|---|---|---|
| 4,143,660 | 3/1979 | Malyshev et al. | 128/303.1 |
| 4,470,407 | 9/1984 | Hussein | 128/6 |
| 4,512,762 | 4/1985 | Spears | 604/21 |
| 4,612,938 | 9/1986 | Dietrich et al. | 128/665 |
| 4,619,261 | 10/1986 | Guerriero | 128/325 |
| 4,633,870 | 1/1987 | Sauer | 128/303.1 |
| 4,672,969 | 6/1987 | Dew | 128/397 |
| 4,676,231 | 6/1987 | Hisazumi et al. | 128/6 |

FOREIGN PATENT DOCUMENTS

| | | | |
|---|---|---|---|
| 182689 | 5/1986 | European Pat. Off. | |
| 0618113 | 8/1978 | U.S.S.R. | 128/303.1 |
| 0618116 | 8/1978 | U.S.S.R. | 128/303.1 |
| 1091933 | 5/1984 | U.S.S.R. | 128/303.1 |
| 2108282 | 5/1983 | United Kingdom | 128/303.1 |

OTHER PUBLICATIONS

Protell et al., Gastroenterology, vol. 74, No. 2, Part 1, Feb. 1978, pp. 257–262.

*Primary Examiner*—Lee S. Cohen
*Attorney, Agent, or Firm*—Wolf, Greenfield & Sacks

[57] ABSTRACT

A method for closing and sealing a puncture at a puncture site in an artery located beneath the skin after a catheter is removed from the puncture. The method includes the steps of applying pressure directly to the artery at the puncture site, and applying laser energy directly to the artery at the puncture site while pressure is applied. The laser energy is sufficient to thermally weld the artery at the puncture site. Preferably, the step of applying pressure directly to the artery includes the steps of advancing a tube having an inflatable balloon at its distal end through the overlying tissue to the punction site, and inflating the balloon. Laser energy is carried thorugh an optical fiber to the balloon and is directed through the wall of the balloon to the puncture site.

14 Claims, 3 Drawing Sheets

METHOD FOR CLOSING AND SEALING AN ARTERY AFTER REMOVING A CATHETER

FIELD OF THE INVENTION

This invention relates to a method for closing an artery to stop bleeding after a catheter or other medical device is removed and, more particularly, to a method for simultaneously applying pressure and laser energy directly to an artery to effect closure and thermal welding of a puncture.

BACKGROUND OF THE INVENTION

In percutaneous transluminal coronary angioplasty, it is customary to introduce a catheter into the femoral artery at an entry site in a patient's leg and to advance the catheter through the artery to the coronary region. The artery, which may be located one half inch or more beneath the skin, is punctured with a needle or similar device, and the catheter is inserted into the artery through a catheter introducer. Catheters typically have a diameter in the range between one millimeter and four millimeters, thus creating a significant puncture in the artery. The catheter is often twisted and otherwise manipulated as it is advanced to the treatment site, thereby causing a further enlargement of the puncture.

When the medical procedure is completed and the catheter is removed from the artery, it has been common practice to simply apply external pressure to the entry site until clotting occurs. The pressure can be applied manually by a nurse or by the use of sandbags. Often, a half hour or more is required before sufficient clotting occurs to remove the applied pressure. The time required to stop bleeding is not an efficient use of medical professional services. Furthermore, a bruise or hematoma often forms at the entry site, since internal bleeding of the punctured artery continues until clotting blocks the puncture.

A technique for coronary angioplasty wherein laser energy is directed through the wall of an inflated balloon in a stenosed region of an artery is disclosed in European Patent Application No. 182,689, published May 28, 1986. The laser energy fuses together fragmented segments of tissue in the stenosed region. U.S. Pat. Ser. No. 4,470,407, issued Sept. 11, 1984 to Hussein, discloses a laser endoscope having a transparent balloon and optical fiber means to irradiate the lumen of a body cavity such as a blood vessel, with laser energy. U.S. Pat. Ser. No. 4,672,969 issued June 16, 1987 to Dew, discloses a laser healing method in which a laser beam is used to heat biological tissue to form a "biological glue". Among the objects of the Dew patent is to provide an improved wound closure technique. However, none of the prior art known to applicant discloses a method for closing and sealing a puncture in an artery located beneath the skin after a catheter is removed from the puncture.

It is a general object of the present invention to provide an improved method for closing and sealing a puncture in an artery after a catheter or other medical device is removed from the puncture.

It is another object of the present invention to reduce the time required for treating a puncture in an artery after a catheter is removed from the puncture.

It is a further object of the present invention to provide a method for closing and sealing a puncture in an artery in which hematoma formation is reduced.

It is a further object of the present invention to provide a method for closing and sealing a puncture in an artery utilizing the simultaneous application of pressure and laser energy directly to the puncture site.

SUMMARY OF THE INVENTION

According to the invention, these and other objects and advantages are achieved in a method for closing and sealing a puncture at a puncture site in an artery located beneath the skin after a medical device such as a catheter is removed from the puncture. The method comprises the steps of applying pressure directly to the artery at the puncture site, the pressure being sufficient to substantially close the puncture, and applying laser energy directly to the artery at the puncture site while pressure is applied. The laser energy is sufficient to thermally weld the artery at the puncture site.

Preferably, the step of applying pressure directly to the artery includes the steps of advancing a rigid or semi-rigid tube having an inflatable balloon at its distal end through overlying tissue to the puncture site, and inflating the balloon. Pressure applied to the tube is transferred through the balloon to the puncture site. In a preferred embodiment, the tube carrying the balloon is advanced through the same introducer that was used for introduction of the catheter. The step of applying laser energy directly to the artery includes the step of directing laser energy through an optical fiber that passes through the tube and terminates in the balloon. The laser energy passes through the wall of the inflated balloon and causes sufficient heating of the puncture site to thermally weld the artery and seal the puncture.

The laser energy applied to the artery through the balloon wall is sufficient to denature and crosslink collagen in the artery wall without removing tissue. The laser energy preferably has a penetration depth sufficient to thermally weld the artery wall, while avoiding coagulation of blood in the artery. A preferred laser wavelength range is 1.4 to 2.5 micrometers.

BRIEF DESCRIPTION OF THE DRAWINGS

For a better understanding of the present invention together with other and further objects, advantages and capabilities thereof, reference is made to the accompanying drawings which are incorporated herein by reference and in which.

DETAILED DESCRIPTION OF THE INVENTION

Figure 1:
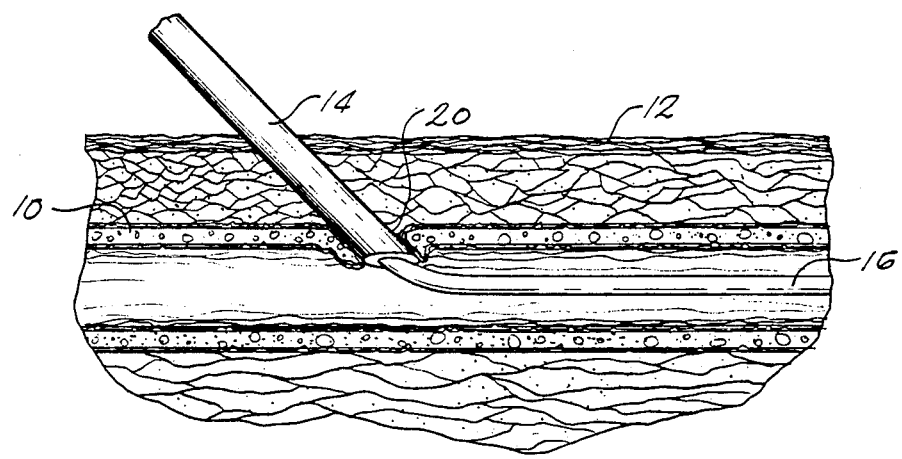
FIG. 1 is an enlarged, partial schematic diagram of a catheter entry site.

A catheter entry site is illustrated in FIG. 1. An artery 10, such as a femoral artery, is located beneath the skin 12 of the patient by about one half inch or more. A needle-like catheter introducer 14 is used to puncture the skin 12 and the underlying tissue and to form a puncture 20 in the artery 10. A catheter 16, usually preceded by a guidewire (not shown), is inserted through the introducer 14 and through the puncture 20. The catheter 16 is then advanced through the artery 10 to the treatment site, which is typically in the coronary region. The use of catheter 16 with catheter introducer 14 is known in the art. A suitable introducer 14 is manufactured and sold by the USCI Division of C.R. Bard, Inc.

Figure 2:
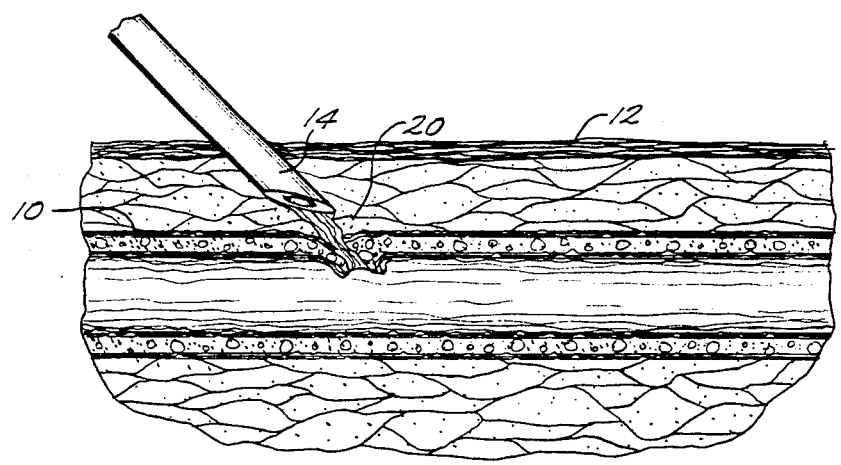
FIG. 2 illustrates the entry site after the catheter is removed.

The diameter of the catheter 16 is typically in the range between one millimeter and four millimeters. As the catheter 16 is advanced to the treatment site, it is pushed, pulled and twisted, frequently causing the puncture 20 to become enlarged to a diameter greater than the catheter diameter. After completion of the medical procedure, the catheter 16 is withdrawn, thereby leaving puncture 20 in artery 10 as shown in FIG. 2. As noted hereinabove, stopping of bleeding from puncture 20 was previously a difficult and time-consuming task.

Figure 4:
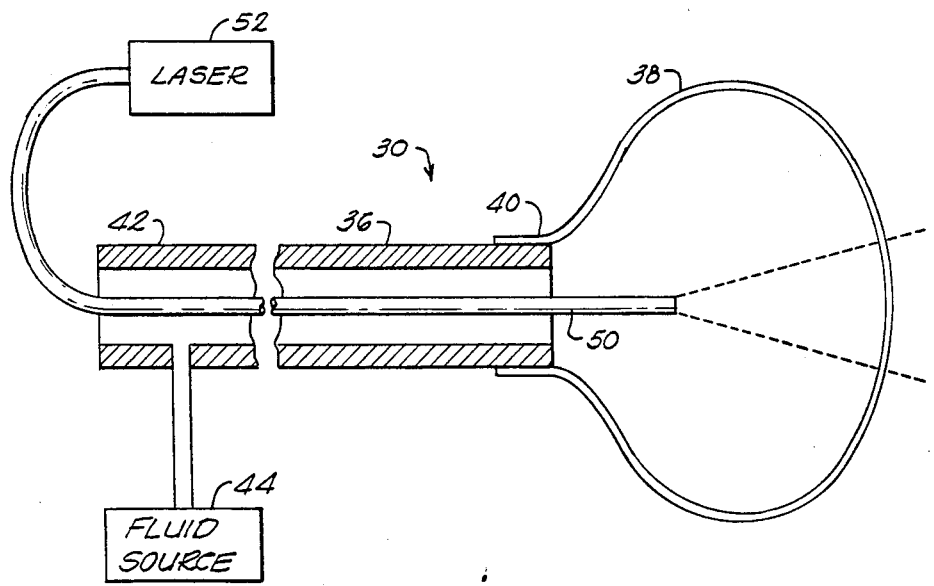
FIG. 4 is a schematic diagram of the apparatus used for closing a puncture in an artery in accordance with the present invention.

In accordance with the present invention, the catheter introducer 14 is left in place after catheter 16 is removed, and a closure device 30 is advanced through introducer 14 to puncture site 32. Alternatively, the catheter introducer 14 can be removed, and the closure device 30 can be advanced to puncture site 32 through the opening left by introducer 14. Referring now to FIG. 4, the closure device 30 includes a rigid or semi-rigid tube 36 having a transparent, inflatable balloon 38 attached to its distal end 40. The balloon 38 must be substantially transparent to laser radiation at the wavelength selected for thermal welding as described hereinafter. The balloon 38 is preferably fabricated from polyethyleneterephthalate (PET) because of its transparency to laser radiation and its resistance to elevated temperatures. Proximal end 42 of tube 36 is coupled to a fluid source 44. The fluid source 44 includes means for supplying a fluid under pressure through tube 36 for inflation of balloon 38, and means for withdrawing the fluid from balloon 38 and deflating it.

An optical fiber 50 passes through tube 36 and terminates within balloon 38. The opposite end of optical fiber 50 is optically coupled by conventional interconnection means (not shown) to a laser 52. When laser 52 is energized, laser energy is guided through optical fiber 50 to balloon 38. The laser radiation passes through the wall of transparent balloon 38 and irridiates the puncture site.

Figure 3:
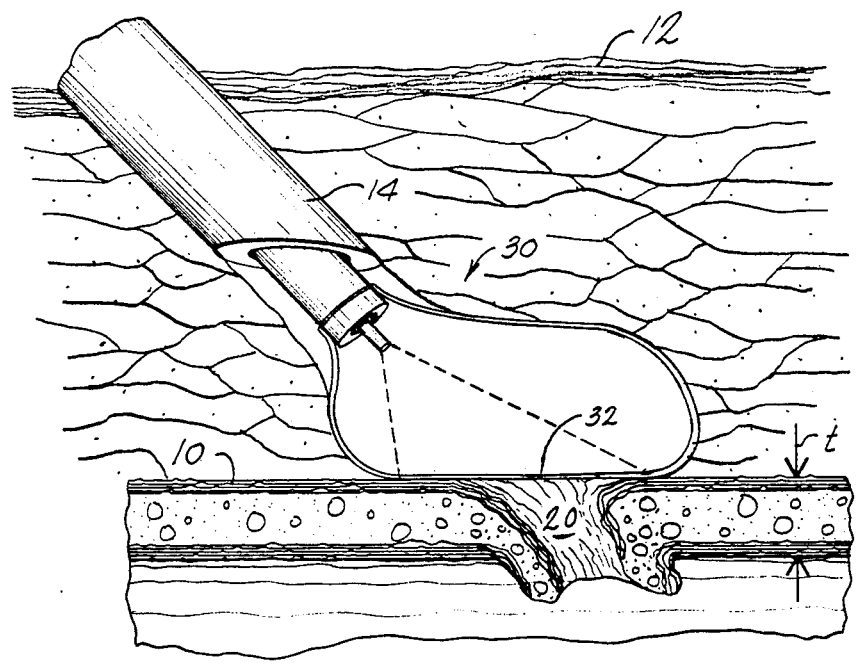
FIG. 3 illustrates application of pressure and laser energy directly to the puncture site in accordance with the present invention.

Referring to FIG. 3, the closure device 30 with the balloon 38 deflated is advanced through introducer 14 to the puncture site 32. The balloon 38 is then inflated by fluid source 44. The fluid source 14 can provide a liquid or a gas for inflation of the balloon 38. Inflated balloon 38 and tube 36 apply pressure to the puncture site 32, causing the edges of the puncture 20 to be generally aligned and closed together. The pressure applied to balloon 38 is preferably in the range of about one to three atmospheres. The laser 52 is then energized, with balloon 38 remaining inflated. Laser energy is guided through the optical fiber 50 and irradiates the puncture site 32. The balloon 38 applies pressure to the puncture site and also displaces blood that otherwise could absorb laser radiation directed at the puncture site.

The laser energy is sufficient to cause thermal welding of the tissue in the artery wall at the puncture site 32, but is below the level sufficient to remove the cells of the artery wall. It is believed that the laser energy causes the collagen in the cells of the artery wall to denature and crosslink. After the artery wall has been thermally welded, the laser 52 is deenergized. Preferably, the balloon 38 is maintained in an inflated state after the laser 52 is deenergized to allow the puncture site 32 to cool. Then, the balloon 38 is deflated, and both the closure device 30 and the catheter introducer 14 are removed. Since the puncture 20 in artery 10 has been closed and sealed, additional bleeding is minor.

It will be understood that the parameters of the laser energy applied to puncture site 32 must be selected to thermally weld the puncture without damaging the tissue or coagulating blood in the artery. The wavelength of the laser energy is preferably chosen to have a penetration depth approximately equal to the thickness, $t$, of the artery wall. When this requirement is met, the energy penetrates the artery wall but does not coagulate blood flowing through the artery 10. The laser energy that penetrates the artery wall thermally welds the sides of the puncture 20 together. Penetrating radiation is preferable to surface heating of the puncture site, since penetrating radiation produces relatively uniform thermal welding of the puncture. Typical artery walls are on the order of 0.5 mm thick, and penetration depths of several hundred micrometers are desired. A preferred wavelength range is 1.4 to 2.5 micrometers. Preferred lasers 52 include holmium, erbium and thulium dopants in a variety of crystalline hosts.

Figure 5A:
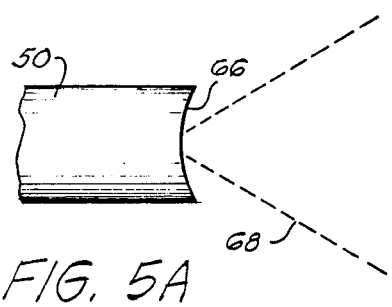
FIGS. 5A–5C illustrate different embodiments of the optical fiber tip.
Figure 5B:
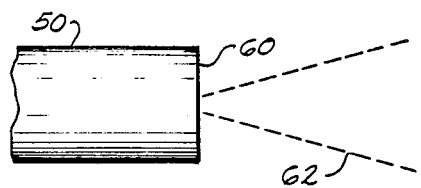
Figure 5C:
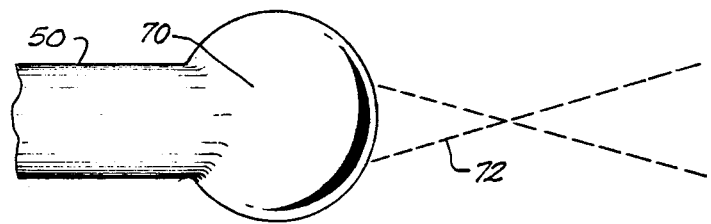

The beam size must be selected to at least cover the puncture 20 and a portion of the artery wall surrounding the puncture 20. The beam size can be controlled by an appropriate configuration of the tip of optical fiber 50, as shown in FIGS. 5A–5C and described hereinafter. The beam size can also be controlled by selecting the angle of incidence of the input beam on optical fiber 50. Typically, the laser 52 has a continuous power level on the order of 1 watt and is energized for a time on the order of one minute or less to achieve the desired thermal welding. In a preferred embodiment, the applied energy density is on the order of 10 watts per square centimeter.

Different optical fiber tip configurations that provide different beam patterns are illustrated in FIGS. 5A–5C. In FIG. 5B, the fiber 50 has a flat tip 60 which provides a somewhat diverging beam 62. As shown in FIG. 5A, the optical fiber 50 can have a concave tip 66 which provides a beam 68 with a wider angle of divergence than the flat tip. When the optical fiber 50 has a convex tip 70 as shown in FIG. 5C, a converging beam 72 is provided. The optical fiber tip configuration can be selected so that the beam size approximately matches the size of the puncture site 32 to be closed and sealed.

The tube 36 is preferably rigid or semi-rigid so that upon inflation of balloon 38, pressure is applied to puncture site 32. A highly flexible tube would deform when balloon 38 was inflated, and pressure would not be applied to the puncture site 32. Preferably, tube 36 is stainless steel having a diameter slightly less than the inside diameter of the introducer, typically on the order of three millimeters.

The technique for closing a puncture in an artery in accordance with the present invention has been described in connection with the use of a catheter. It will be understood that the technique of the invention can be used after removal of any medical device from an artery and can be applied in any situation where an artery or a vein located beneath the skin must be closed and sealed.

While there have been shown and described what are at present considered the preferred embodiments of the present invention, it will be obvious to those skilled in the art that various changes and modifications may be made therein without departing from the scope of the invention as defined by the appended claims.

I claim:

1. A method for closing and sealing a puncture at a puncture site in an artery located beneath the skin, after a medical device is removed from the puncture, comprising the steps of:

applying pressure directly to the artery at the puncture site, said pressure being sufficient to substantially close the puncture, the step of applying pressure including the steps of advancing a tube having an inflatable balloon at its distal end through overlying tissue to the puncture site, and inflating the balloon so that the balloon and the tube apply pressure to the puncture site; and applying laser energy directly to the artery at the puncture site while pressure is applied, said laser energy being sufficient to thermally weld the artery at the puncture site.

2. A method as defined in claim 1 wherein the step of advancing a tube to the puncture site includes the step of advancing the tube through an introducer that was used for introduction of a catheter.

3. A method as defined in claim 1 wherein the step of applying laser energy includes the step of directing laser energy through said tube and through said balloon to effect heating of said artery.

4. A method as defined in claim 3 wherein the step of directing laser energy through said tube includes the step of directing laser energy through an optical fiber that terminates in said balloon.

5. A method as defined in claim 1 wherein the step of applying laser energy includes applying laser energy in a wavelength range of 1.4 to 2.5 micrometers.

6. A method as defined in claim 1 wherein the step of applying laser energy includes applying laser energy having a penetration depth sufficient to thermally weld said puncture while avoiding coagulation of blood in said artery.

7. A method as defined in claim 1 wherein the step of applying pressure includes the step of providing a transparent PET balloon affixed to the distal end of said tube.

8. A method as defined in claim 1 wherein the step of applying laser energy includes applying laser energy having a penetration depth not substantially greater than the thickness of the artery wall.

9. A method as defined in claim 1 wherein said tube has sufficient rigidity to support the pressure applied to said puncture site by said balloon.

10. A method for closing and sealing a puncture at a puncture site in an artery located beneath the skin, after a catheter is removed from the puncture, comprising the steps of:

advancing a tube having an inflatable balloon at its distal end through a catheter introducer to the puncture site;

inflating the balloon so that the balloon and the tube apply pressure directly to the puncture site, said pressure being sufficient to substantially close the puncture; and directing laser energy through said tube and through said balloon to effect direct heating of the puncture site, said laser energy being sufficient to thermally weld the artery at the puncture site.

11. A method as defined in claim 10 wherein the step of directing laser energy includes directing laser energy in a wavelength range of 1.4 to 2.5 micrometers.

12. A method as defined in claim 10 wherein the step of directing laser energy includes applying laser energy having a penetration depth sufficient to thermally weld said puncture while avoiding coagulation of blood in said artery.

13. A method as defined in claim 10 wherein the step of directing laser energy through said tube includes the step of directing laser energy through an optical fiber that terminates in said balloon.

14. A method as defined in claim 10 wherein the step of directing laser energy includes applying laser energy having a penetration depth not substantially greater than the thickness of the artery wall.

* * * * *